United States Patent
Usuda et al.

(10) Patent No.: US 9,126,000 B2
(45) Date of Patent: Sep. 8, 2015

(54) ARTIFICIAL VENTILATION APPARATUS

(75) Inventors: Yutaka Usuda, Kanagawa (JP); Naofumi Kobayashi, Tokyo (JP); Shinji Yamamori, Tokyo (JP); Yasushi Nagai, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 13/035,947

(22) Filed: Feb. 26, 2011

(65) Prior Publication Data

US 2011/0209703 A1 Sep. 1, 2011

Related U.S. Application Data

(60) Provisional application No. 61/320,731, filed on Apr. 3, 2010.

(30) Foreign Application Priority Data

Feb. 26, 2010 (JP) .................................. 2010-042379
Mar. 17, 2010 (JP) .................................. 2010-060756

(51) Int. Cl.
*A61M 16/00* (2006.01)
*A61M 16/08* (2006.01)
(Continued)

(52) U.S. Cl.
CPC .......... *A61M 16/0051* (2013.01); *A61M 16/107* (2014.02); *A61M 16/1065* (2014.02);
(Continued)

(58) Field of Classification Search
CPC ............ A61M 16/0051; A61M 16/12; A61M 2016/0039; A61M 2016/1025; A61M 16/00
USPC ............ 128/204.22, 204.23, 203.12, 205.12, 128/203.25, 202.22, 205.23, 204.21, 128/200.24, 204.18, 205.11, 205.16, 128/205.13, 205.18; 600/529–538
See application file for complete search history.

(56) References Cited

U.S. PATENT DOCUMENTS 4,537,190 A   8/1985  Caillot et al.
4,619,269 A * 10/1986  Cutler et al. .................. 600/532
(Continued)

FOREIGN PATENT DOCUMENTS

CN    101596342 A    12/2009
JP    58-105762 A    8/1985
(Continued)

OTHER PUBLICATIONS

Parallax C02 Gas Sensor (#27929) Data Sheet dated Feb. 25, 2010.*
(Continued)

*Primary Examiner* — Tan-Uyen (Jackie) T Ho
*Assistant Examiner* — Mark Wardas
(74) *Attorney, Agent, or Firm* — Kenealy Vaidya LLP

(57) ABSTRACT

An artificial ventilation apparatus includes: a connecting portion which is connected to a respiratory system of a patient; an inspiratory circuit which is a flow path for flowing a gas from a ventilator to the connecting portion; an expiratory circuit which is a flow path for guiding a gas exhausted from the connecting portion to an exhaust portion of the ventilator; an expiratory valve which blocks a flow of a gas from the exhaust portion toward the connecting portion; a carbon dioxide concentration sensor which is disposed in a circuit that is provided at a downstream side of the expiratory valve and which detects a carbon dioxide concentration; and an alarm outputting unit which outputs an alarm based on an output of the carbon dioxide concentration sensor.

4 Claims, 7 Drawing Sheets

(51) Int. Cl.
*A61M 16/10* (2006.01)
*A61M 16/20* (2006.01)

(52) U.S. Cl.
CPC ........ *A61M16/0808* (2013.01); *A61M 16/1055* (2013.01); *A61M 16/208* (2013.01); *A61M 2016/0027* (2013.01); *A61M 2205/502* (2013.01); *A61M 2205/581* (2013.01); *A61M 2205/583* (2013.01); *A61M 2230/205* (2013.01); *A61M 2230/30* (2013.01); *A61M 2230/42* (2013.01); *A61M 2230/432* (2013.01); *A61M 2230/50* (2013.01)

(56) References Cited

U.S. PATENT DOCUMENTS

| | | | | |
|---|---|---|---|---|
| 5,092,326 | A * | 3/1992 | Winn et al. | 128/205.13 |
| 5,094,235 | A * | 3/1992 | Westenskow et al. | 128/204.22 |
| 5,603,316 | A * | 2/1997 | Coufal et al. | 128/204.23 |
| 6,046,441 | A * | 4/2000 | Daffron | 219/506 |
| 6,221,012 | B1 * | 4/2001 | Maschke et al. | 600/301 |
| 2007/0027390 | A1 * | 2/2007 | Maschke et al. | 600/425 |
| 2007/0062540 | A1 * | 3/2007 | Murray-Harris | 128/207.29 |
| 2007/0068518 | A1 | 3/2007 | Urias et al. | |
| 2008/0091117 | A1 | 4/2008 | Choncholas et al. | |
| 2008/0121232 | A1 * | 5/2008 | Cewers | 128/204.22 |
| 2011/0201957 | A1 * | 8/2011 | Zhou et al. | 600/532 |

FOREIGN PATENT DOCUMENTS

| | | |
|---|---|---|
| JP | 6-20535 B | 6/1994 |
| JP | 2002-11100 A | 1/2002 |

OTHER PUBLICATIONS

Extended European Search Report Jun. 30, 2011.
Chinese Office Action for the related Chinese Patent Application No. 201110046494.3 dated Mar. 24, 2014.
Chinese Office Action for the related Chinese Patent Application No. 201110046494.3 dated Feb. 28, 2015.

* cited by examiner

ARTIFICIAL VENTILATION APPARATUS

BACKGROUND OF THE INVENTION

The present invention relates to an artificial ventilation apparatus including a carbon dioxide concentration sensor.

An artificial ventilation apparatus is equipped with functions of detecting a non- or hypo-ventilated state of the patient due to malfunction of a ventilator or an abnormality of a respiratory circuit, and generating an alarm. Particularly, it is said that End-tidal CO2 (EtCO2) monitoring is useful because it is possible to check that the patient actually performs gas exchange.

An EtCO2 measuring mechanism mounted on an artificial ventilation apparatus or on a patient monitoring apparatus other than an artificial ventilation apparatus is configured as shown in FIG. 4.

The apparatus shown in FIG. 4 is a related-art artificial ventilation apparatus, and configured in the following manner. A ventilator 80 is connected to the respiratory system of the patient A through an inspiratory valve 82 which is a one-way valve, an infection prevention filter 86, a heating and humidifying device 87, a water trap 88, and a respiratory circuit 81. The respiratory system of the patient A is connected to an exhaust portion 91 of the ventilator 80 through the respiratory circuit 81, a water trap 89, an infection prevention filter 90, and an expiratory valve 83 which is a one-way valve. A respiratory gas is sent from the ventilator 80 to the patient through the inspiratory valve 82, and the expiratory gas of the patient is discharged from an exhaust port 91A through the expiratory valve 83 and the exhaust port 91.

In the related-art artificial ventilation apparatus, a carbon dioxide concentration sensor 84 is disposed at a position near the mouth of the patient A, to measure the EtCO2 of the patient A, thereby monitoring the situation of the gas exchange of the patient A. The devices and appliances which include the carbon dioxide concentration sensor 84, and which exist between the patient A and the ventilator 80, i.e., the infection prevention filters 86, 90, the heating and humidifying device 87, the water traps 88, 89, and the respiratory circuit 81 are configured so as to be easily attached and detached, in order to enable replacement, sterilization, or replacement for every patient (for example, see FIG. 1 of JP-UM-B-6-20535).

The ventilator 80 includes a power supply portion 85 which supplies an electric power to various portions of the ventilator 80. The power supply portion 85 performs a necessary power supply also on the carbon dioxide concentration sensor 84. However, some of simple ventilators which are operated manually or by an additional pressure source or the like do not include a power supply portion.

There is a related-art artificial ventilation apparatus which detects the carbon dioxide concentration by using the side stream method, in which the volume of carbon dioxide is calculated by a carbon dioxide concentration detector that is connected through a sampling tube to the middle of an expiratory circuit located upstream of an expiratory circuit, and a flow rate meter that is connected to an inspiratory circuit (see JP-A-2002-11100).

In the related-art apparatus shown in FIG. 4 or JP-UM-B-6-20535, as described above, many portions which can be easily attached and detached exist between the ventilator 80 and the patient A, and hence the probability that a connecting portion is disconnected is correspondingly increased. Particularly, there is a possibility that disconnection of an inspiratory circuit portion may seriously affect the patient. Therefore, there is a very cumbersome problem in that it is necessary to check that the carbon dioxide concentration sensor 84 and the like are surly attached, so that a ventilation failure in the patient due to disconnection of a connecting portion, malfunction of the alarm due to disconnection of the sensor, a ventilation failure in the patient due to the malfunction, or the like does not occur.

The respiratory gas is humidified by the heating and humidifying device 87, and the carbon dioxide concentration sensor 84 is disposed at the position near the mouth of the patient A. Therefore, dew condensation easily occurs in circuits in the vicinity of the carbon dioxide concentration sensor 84. When dew condensation once occurs, normal detection of the carbon dioxide concentration by the carbon dioxide concentration sensor 84 is hardly conducted. This may cause malfunction of an alarm or the like.

In the case where the patient performs spontaneous respiration, when the expiratory circuit (for example, the connecting portion of the infection prevention filter 90) of the respiratory circuit 81 is disconnected, or when the inspiratory circuit (for example, the connecting portion of the infection prevention filter 86) of the respiratory circuit 81 is disconnected, the respiratory gas is not sent to the patient. However, the carbon dioxide concentration sensor 84 detects carbon dioxide produced by spontaneous respiration of the patient, and hence the disconnection cannot be detected by the carbon dioxide concentration sensor 84. In the case where the patient does not perform spontaneous respiration, when the inspiratory circuit is disconnected, the respiratory gas cannot be supplied, and hence the detection value of the carbon dioxide concentration sensor 84 becomes abnormal, so that the abnormal state can be detected. By contrast, when the expiratory circuit is disconnected, a case where the disconnection cannot be detected may be possible depending on the portion where the disconnection occurs. If the disconnected portion is near the expiratory valve 83, namely, the pipe resistance of the expiratory circuit is large. This allows the respiratory gas to be sent to the patient, and carbon dioxide is detected by the carbon dioxide concentration sensor 84. Therefore, there is a possibility that the disconnection cannot be detected.

In the specification, the term "disconnection can be detected" means that, when disconnection occurs, the carbon dioxide concentration detected by the carbon dioxide concentration sensor becomes an abnormal state, and not always means that the disconnected portion is identified. The term "disconnection cannot be detected" means that the carbon dioxide concentration detected by the carbon dioxide concentration sensor does not become abnormal.

In the related-art apparatus shown in FIG. 4, the single power supply portion 85 supplies an electric power to the ventilator 80 and the carbon dioxide concentration sensor 84. When the power supply portion 85 does not function, therefore, the ventilator 80 does not operate, and at the same time also the carbon dioxide concentration sensor 84 does not work, with the result that an alarm is not generated, and the abnormality cannot be known. Usually, a simple ventilator which does not include such a power supply portion fails to have a function of monitoring the carbon dioxide concentration.

In the related-art apparatus disclosed in JP-A-2002-11100, the carbon dioxide concentration detector is connected to the side of the expiratory circuit, but the sampling tube for the expiratory gas is connected to the upstream side of the expiratory valve. The sampling tube and the carbon dioxide concentration detector must be configured so as to be easily attached and detached, in order to enable replacement, sterilization, or replacement for every patient. Therefore, also the apparatus has a very cumbersome problem in that it is necessary to check that the carbon dioxide concentration detector and the like are surly attached, so that a ventilation failure in the patient due to disconnection of a connecting portion, malfunction of the alarm due to disconnection of the sensor, a ventilation failure in the patient due to the malfunction, or the like does not occur.

SUMMARY

It is therefore an object of the invention to provide an artificial ventilation apparatus in which the number of portions that can be easily attached and detached is decreased, so that the time period required for inspecting connecting portions is shortened, and the probability of disconnection of the connecting portions is decreased, thereby enhancing the safety.

It is another object of the invention to provide an artificial ventilation apparatus in which an effect of dew condensation on a carbon dioxide concentration sensor is reduced.

It is another object of the invention to provide an artificial ventilation apparatus in which, not only in the case where spontaneous respiration is not performed, but also in the case where spontaneous respiration is performed, disconnection of a respiratory circuit can be detected, and furthermore the disconnected portion can be identified.

It is another object of the invention to provide an artificial ventilation apparatus in which, even when a supply of an electric power to a ventilator is interrupted for any cause, or even in a ventilator that does not include a power supply portion and a carbon dioxide concentration sensor, a carbon dioxide concentration sensor operates, and in case of necessary an alarm is generated, so that the abnormality can be known.

It is another object of the invention to provide an artificial ventilation apparatus which can analyze in detail the state of the apparatus including a respiratory circuit, and that of the patient.

In order to achieve the object, according to the invention, there is provided an artificial ventilation apparatus comprising: a connecting portion which is connected to a respiratory system of a patient; an inspiratory circuit which is a flow path for flowing a gas from a ventilator to the connecting portion; an expiratory circuit which is a flow path for guiding a gas exhausted from the connecting portion to an exhaust portion of the ventilator; an expiratory valve which blocks a flow of a gas from the exhaust portion toward the connecting portion; a carbon dioxide concentration sensor which is disposed in a circuit that is provided at a downstream side of the expiratory valve and which detects a carbon dioxide concentration; and an alarm outputting unit which outputs an alarm based on an output of the carbon dioxide concentration sensor.

The artificial ventilation apparatus may further include a dedicated power supply portion which supplies an electric power to the carbon dioxide concentration sensor and the alarm outputting unit.

The carbon dioxide concentration sensor may be disposed in an exhaust port of the exhaust portion.

The alarm outputting unit may include a state determining unit which obtains information, which includes at least one of apparatus information of the artificial ventilation apparatus and biological information of the patient, the state determining unit which, based on obtained information and the output of the carbon dioxide concentration sensor, determines whether a state, which includes at least one of an apparatus state of the artificial ventilation apparatus and a patient state of the patient, is abnormal or not.

DETAILED DESCRIPTION OF EMBODIMENTS

Figure 1:
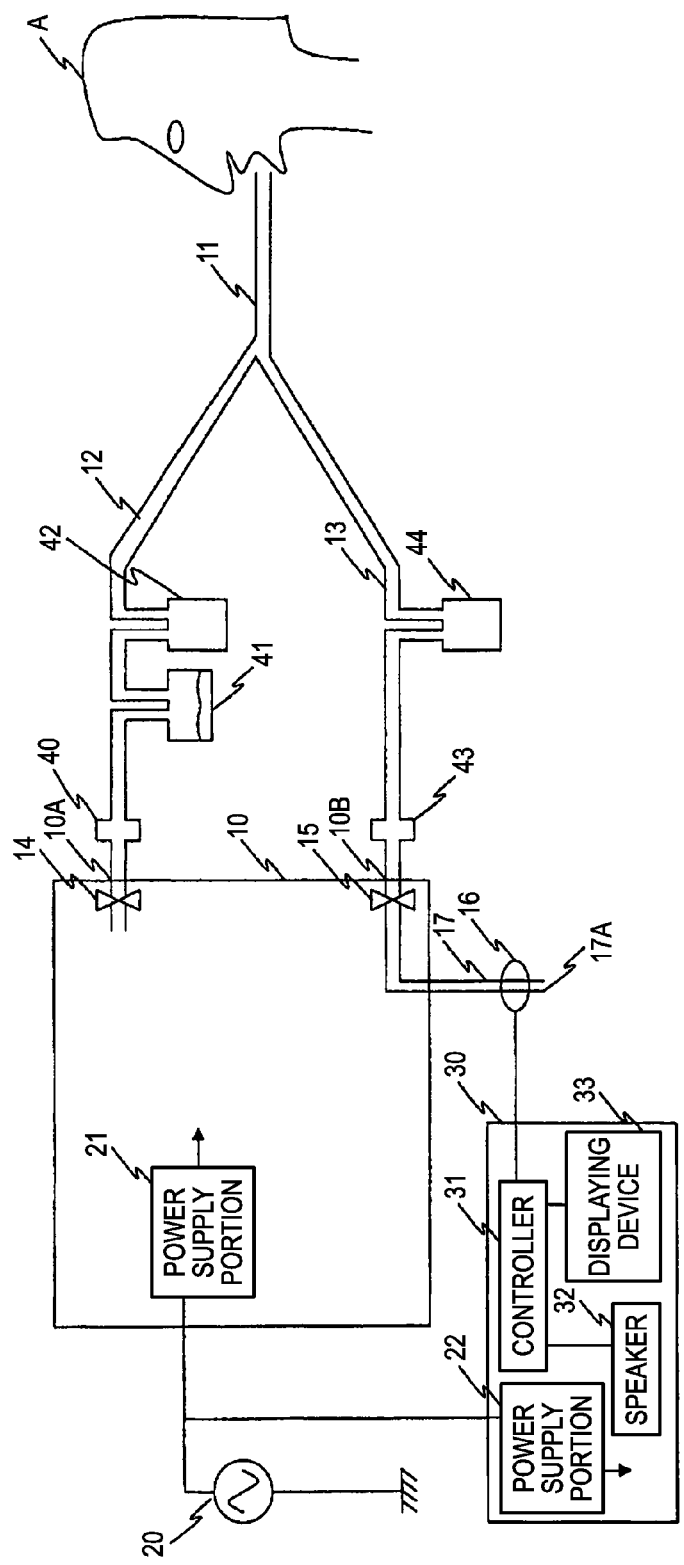
FIG. 1 is a block diagram showing the configuration of a first embodiment of the artificial ventilation apparatus of the invention.

Hereinafter, embodiments of the artificial ventilation apparatus of the invention will be described with reference to the accompanying drawings. In the figures, the identical components are denoted by the same reference numerals, and duplicated description will be omitted. FIG. 1 shows the configuration of an artificial ventilation apparatus of a first embodiment. The artificial ventilation apparatus includes a ventilator 10 which outputs a gas having a required oxygen concentration for artificial ventilation, at a required pressure.

A connecting portion 11 which is connected to the respiratory system of the patient A is attached to the respiratory system. The connecting portion 11 is configured by a mask, a conduit tube intubated into the trachea, or the like. An inspiratory circuit 12 which is a flow path for flowing the gas from the ventilator 10 to the connecting portion 11 connects between a gas outlet 10A of the ventilator 10 and the connecting portion 11. In the inspiratory circuit 12, an infection prevention filter 40 which traps bacteria is disposed in the vicinity of the gas outlet 10A, and a heating and humidifying device 41 which humidifies the gas for artificial ventilation, and a water trap 42 which traps excess water of the gas for artificial ventilation are disposed in adequate places.

An expiratory circuit 13 which is a flow path for guiding the gas exhausted from the connecting portion 11 to an exhaust portion 17 of the ventilator 10 connects between a gas inlet 10B of the ventilator 10 and the connecting portion 11. In the expiratory circuit 13, an infection prevention filter 43 which traps bacteria is disposed in the vicinity of the gas inlet 10B, and a water trap 44 which traps water of the exhausted gas is disposed in an adequate place.

In the ventilator 10, an inspiratory one-way valve 14 is disposed in the vicinity of the gas outlet 10A. The inspiratory one-way valve 14 has functions of allowing only the gas flow which is directed from the ventilator 10 to the connecting portion 11, and blocking the flow from the connecting portion 11.

In the ventilator 10, furthermore, an expiratory circuit one-way valve 15 is disposed in the vicinity of the gas inlet 10B. The expiratory circuit one-way valve 15 has functions of allowing only the gas flow which is directed from the connecting portion 11 to the ventilator 10, and blocking the flow toward the connecting portion 11. The inspiratory one-way valve 14 and the expiratory circuit one-way valve 15 cooperate with each other to participate in the ventilation operation of the ventilator 10 which is performed on the patient A.

A carbon dioxide concentration sensor 16 is disposed in a circuit which is downstream of the expiratory circuit one-way valve 15. Specifically, the carbon dioxide concentration sensor 16 is disposed at a position near an exhaust port 17A of the exhaust portion 17 which extends from the expiratory circuit one-way valve 15 to the atmosphere. The position of the carbon dioxide concentration sensor 16 may be outside or inside the ventilator 10.

The carbon dioxide concentration sensor 16 is firmly fixed to the exhaust portion 17, and configured so that there is no possibility that the sensor is disconnected from the circuit. When the carbon dioxide concentration sensor 16 is attached to the exhaust port 17A outside the ventilator 10, limitations of the attachment space are not largely imposed on the apparatus. Therefore, the sensor can be later attached to an existing artificial ventilation apparatus in a relatively easy manner.

A power supply portion 21 (a first power supply portion) is disposed in the ventilator 10. The power supply portion 21 receives a power supply from an external power supply (for example, a power supply which is backed up in an emergency) 20, converts to a required voltage, and then supplies the electric power to necessary circuits. The artificial ventilation apparatus has a power supply portion (second power supply portion) 22 for the sensor. The power supply portion 22 receives a power supply from the external power supply 20, converts to a required voltage, and then supplies the electric power to the carbon dioxide concentration sensor 16.

The power supply portion 22 is disposed in a monitoring apparatus portion 30. The monitoring apparatus portion 30 includes a controller 31, speaker 32, and displaying device 33 such as an LED which constitute an alarm outputting unit. The controller 31, the speaker 32, and the displaying device 33 receive the power supply from the power supply portion 22 to operate. The controller 31, the speaker 32, and the displaying device 33 output an alarm based on the output of the carbon dioxide concentration sensor 16. The monitoring apparatus portion may be configured so that, in the normal state, the controller 31 controls the displaying device 33 so as to display the EtCO2 on the displaying device 33 based on the output of the carbon dioxide concentration sensor 16.

Figure 2:
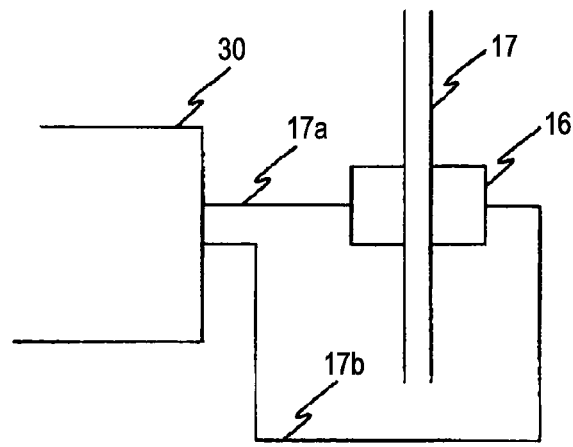
FIG. 2 is a block diagram showing the configuration of a portion of the artificial ventilation apparatus of the invention.

A mainstream system may be employed in which, as shown in FIG. 2, the carbon dioxide concentration sensor 16 is disposed in the exhaust portion 17, and connected to the monitoring apparatus portion 30 through a signal line 17a and a power supply line 17b.

Figure 3:
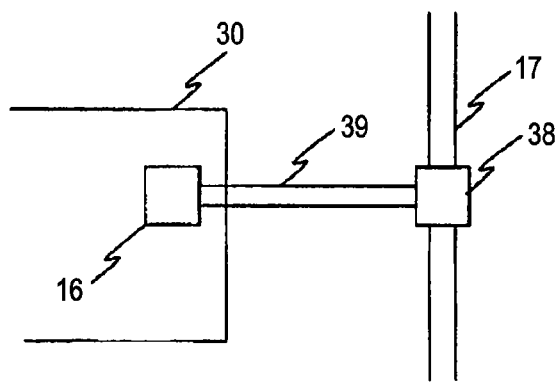
FIG. 3 is a block diagram showing the configuration of a portion of the artificial ventilation apparatus of the invention.
Figure 4:
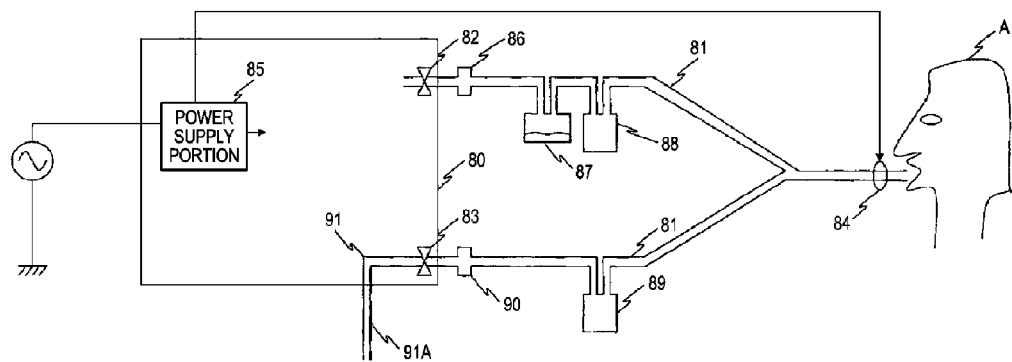
FIG. 4 is a block diagram showing the configuration of an artificial ventilation apparatus of the invention of a related art example.

Alternatively, a sidestream system may be employed in which, as shown in FIG. 3, the carbon dioxide concentration sensor 16 is disposed in the monitoring apparatus portion 30, and the expiratory gas is guided to the carbon dioxide concentration sensor 16 from a branch pipe 38 coupled to the exhaust portion 17, through a sampling tube 39.

In FIGS. 2 and 3, the monitoring apparatus portion 30 is disposed outside the ventilator 10. Alternatively, the portion may be inside the ventilator 10.

In the thus configured artificial ventilation apparatus, in response to an operation of turning ON the power supply, the operations of the ventilator 10 and the monitoring apparatus portion 30 are started to supply the gas from the ventilator 10 to the patient A, and discharge the expiratory gas through the expiratory circuit 13. At this time, the detection of the carbon dioxide concentration by the carbon dioxide concentration sensor 16, and the display on the displaying device 33 are performed. When circuit disconnection occurs in the inspiratory circuit 12 or the expiratory circuit 13, a large change is produced in the carbon dioxide concentration detected by the carbon dioxide concentration sensor 16 which is disposed in the terminal end of the circuit, and an alarm is output in, for example, the speaker 32 and the displaying device 33. Even when circuit disconnection occurs at any position, therefore, this can be easily detected, and hence the safety is high.

Since the carbon dioxide concentration sensor 16 is firmly attached to the exhaust portion 17, sensor disconnection does not occur, and hence the safety is high. Even when components including the carbon dioxide concentration sensor 16 and the sampling tube 39 are contaminated by the expiratory of the patient, a contaminated gas or the like does not flow toward the connecting portion 11 because these components are downstream of the infection prevention filter 43 and the expiratory circuit one-way valve 15. Therefore, it is possible to realize a maintenance-free apparatus in which components including the carbon dioxide concentration sensor 16 and the sampling tube 39 are not required to be replaced or sterilized, with the result that the user can be relieved of cumbersome works of replacement and sterilization, and the cost can be reduced.

Moreover, the apparatus has the configuration where the power supply portion 22 which is different from the power supply portion 21 for the ventilator 10 supplies an electric power to the carbon dioxide concentration sensor 16 and in case of necessary an alarm is output. Also in the case where an abnormality occurs in the power supply portion 21 for the ventilator 10, the carbon dioxide concentration sensor 16 remains to operate, and surely detects the abnormality, and the speaker 32 and the displaying device 33 output an alarm to inform of the abnormality. Also in this point, the high safety is ensured.

Figure 5:
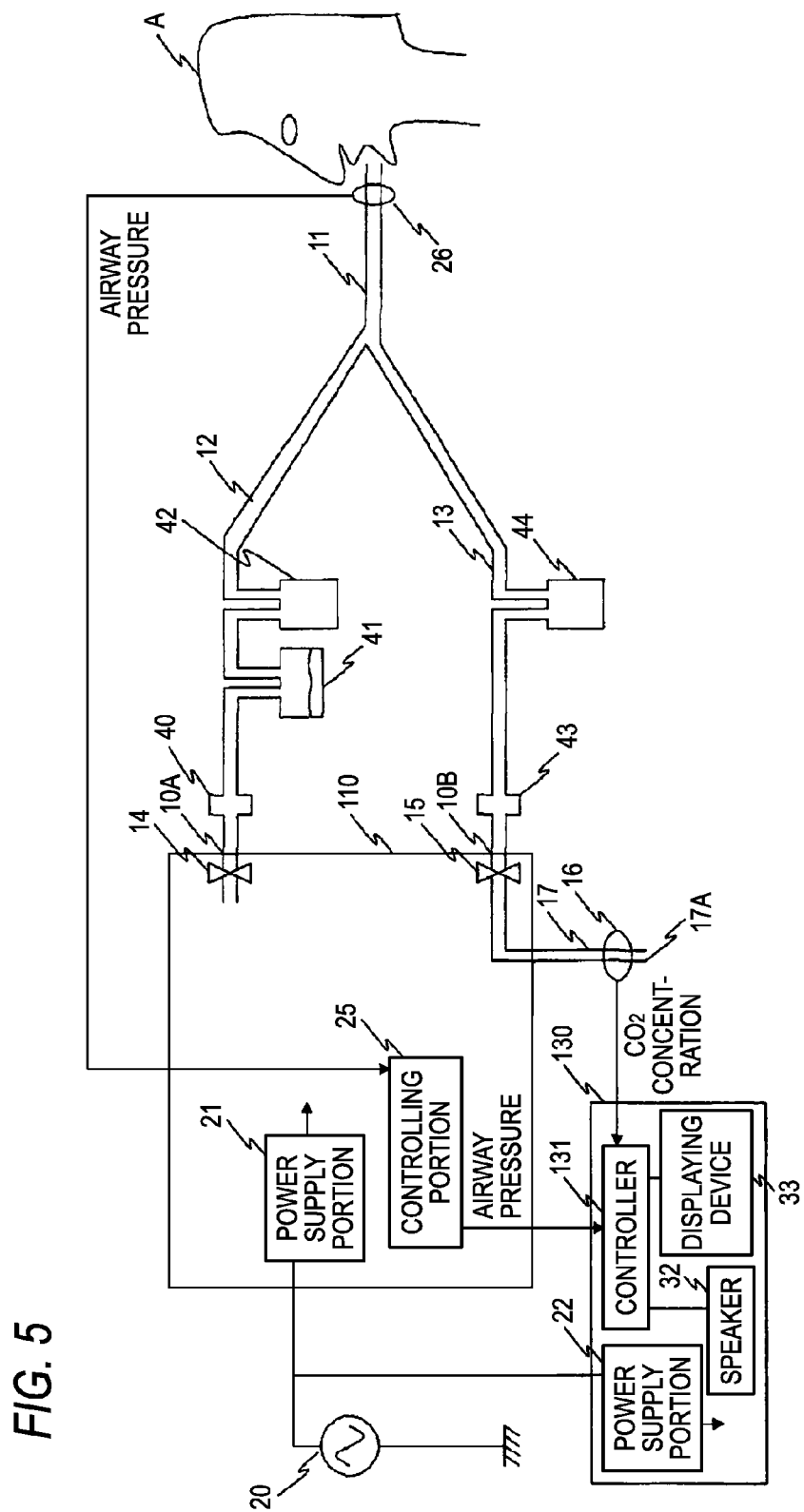
FIG. 5 is a block diagram showing the configuration of a second embodiment of the artificial ventilation apparatus of the invention.

FIG. 5 shows the configuration of an artificial ventilation apparatus of a second embodiment. In the artificial ventilation apparatus, a ventilator 110 includes a controlling portion 25. The controlling portion 25 is similar to a corresponding related-art portion, i.e., controls the operation of the apparatus based on biological information of the patient A and apparatus information of the apparatus, monitors the patient A and the apparatus to display required parameters, and, in case of abnormality, generates an alarm. The biological information means information related to the living body, such as the arterial oxygen saturation, the blood pressure, the body temperature, the respiratory rate, and the airway pressure. In FIG. 5, only a pressure sensor 26 which is disposed in the connecting portion 11 in order to obtain information of the airway pressure is shown.

The apparatus information of the apparatus is operation information of the ventilator 110, information such as the pressure and temperature in the respiratory circuit, information such as the output voltage and current of the power supply portion 21, and all other information related to the apparatus, and includes the time of use, etc. The apparatus information is not shown in FIG. 5.

In the embodiment, information of the airway pressure of the patient A is given from the controlling portion 25 of the ventilator 110 to a controller 131 of a monitoring apparatus portion 130. Also, information of the carbon dioxide concentration is given from the carbon dioxide concentration sensor 16 to the controller 131. Based on the airway pressure information and the carbon dioxide concentration information, the controller 131 determines whether the apparatus state and the patient state are normal or not. The embodiment is configured so that a result of the determination is displayed on the displaying device 33 which is a displaying unit, and, if the determination result shows an abnormal state, an alarm is output by using the speaker 32.

In the above-described configuration, the controlling portion 25 operates on the electric power supplied from the power supply portion 21, and the controller 131 operates on the electric power supplied from the power supply portion 22. The other configuration of the artificial ventilation apparatus of the second embodiment is identical with that of the apparatus of the first embodiment.

The thus configured artificial ventilation apparatus monitors the apparatus state and the patient state in the following manner. In the case where the carbon dioxide concentration sent from the carbon dioxide concentration sensor 16, and the airway pressure sent from the pressure sensor 26 regularly change in accordance with the respiration operation of the patient A (in the case where the patient A does not perform spontaneous respiration, the operation of the ventilator 110), the controller 131 determines that the apparatus state and the patient state are normal, and displays a message indicating this on the displaying device 33. When the carbon dioxide concentration and/or the airway pressure shows an abnormal state as described in detail below, the controller 131 determines that the apparatus is in an abnormal state, displays a message indicating this on the displaying device 33, and, as required, outputs an alarm from the speaker 32.

Next, estimation will be described in which, in the case where disconnection occurs in the inspiratory circuit 12 and the expiratory circuit 13, the disconnection place is eliminated based on the carbon dioxide concentration and the airway pressure. In the following description, the case where the disconnection independently occurs will be described. Also in the case where an abnormality other than the above is generated or a plurality of abnormalities including the above-described disconnection combinedly occur, the case where the carbon dioxide concentration and the airway pressure show similar tendencies may be possible. Therefore, the term "disconnection detection" which will be used in the following description means estimation that there is a possibility that disconnection occurs in the place.

Figure 6A:
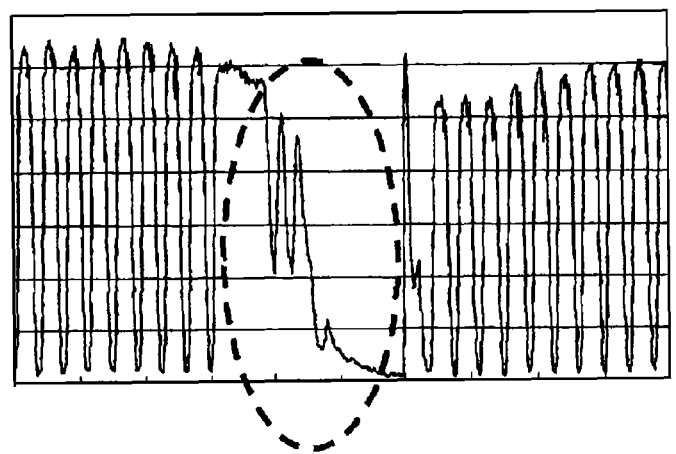
FIG. 6A shows the waveform of the carbon dioxide concentration in the case where an inspiratory circuit in the second embodiment of the artificial ventilation apparatus of the invention is disconnected.
Figure 6B:
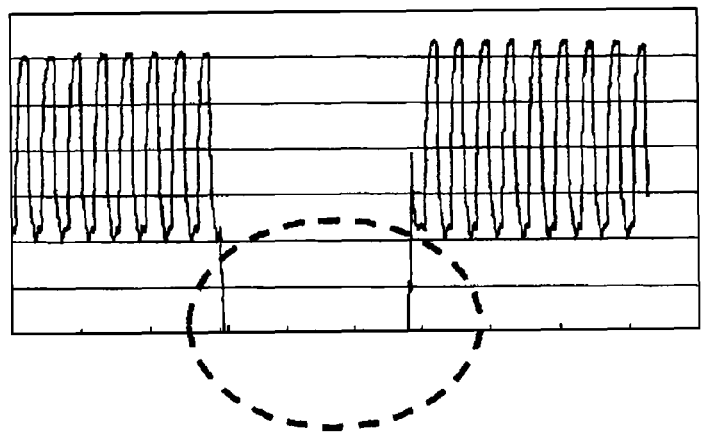
FIG. 6B shows the waveform of the airway pressure in the case.
Figure 7A:
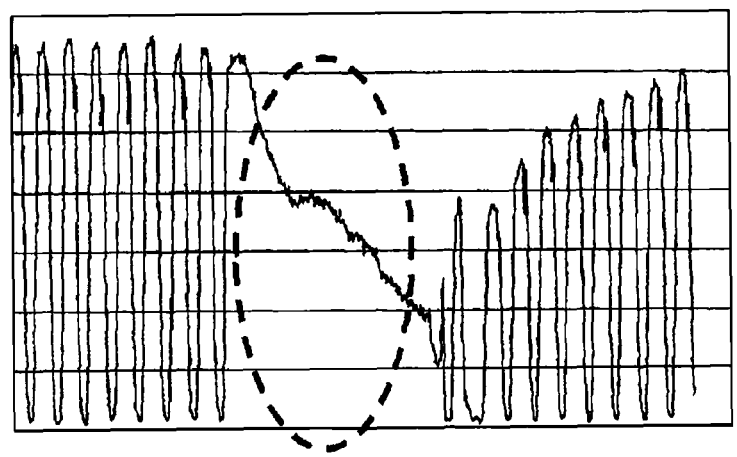
FIG. 7A shows the waveform of the carbon dioxide concentration in the case where an expiratory circuit in the second embodiment of the artificial ventilation apparatus of the invention is disconnected.
Figure 7B:
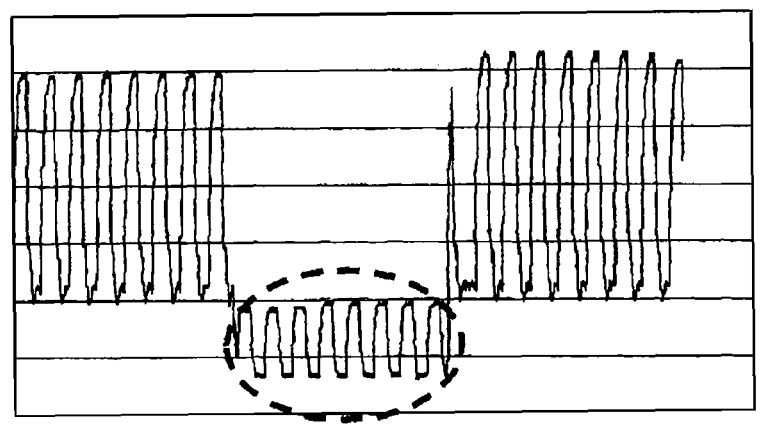
FIG. 7B shows the waveform of the airway pressure in the case.

FIGS. 6A and 6B show waveforms of the carbon dioxide concentration and the airway pressure in the case where disconnection occurs in the inspiratory circuit 12, and FIGS. 7A and 7B show waveforms of the carbon dioxide concentration and the airway pressure in the case where disconnection occurs in the expiratory circuit 13, respectively. In the graphs, the abscissa indicates the elapsed time. In this case, with respect to the carbon dioxide concentration, a rectangular wave due to respiration is disturbed and stops as indicted by the enclosing circles in FIGS. 6A and 7A. FIGS. 6A and 7A show examples of the measurement result, and such a waveform is not always produced. In any case, the disturbance and stoppage of a rectangular wave are observed. From only these waveforms, however, the place where a trouble occurs cannot be identified.

By contrast, with respect to the airway pressure, in the case where disconnection occurs in the inspiratory circuit 12, a rectangular wave stops and transits to a flat waveform as indicted by the enclosing circle in FIG. 6B. In the case where disconnection occurs in the expiratory circuit 13, a rectangular wave having a low amplitude (P-P value) is formed as indicted by the enclosing circle in FIG. 7B. This is caused by the fact that the airway pressure is changed by the pipe resistance of the expiratory circuit 13.

By using the obtained information or the airway pressure and the carbon dioxide concentration, the controller 131 determines whether the place of disconnection is in the inspiratory circuit 12 or in the expiratory circuit 13. When the carbon dioxide concentration is smaller than a predetermined threshold, and lowering of the airway pressure to or below a predetermined value, and nonexistence of pulses in the lowered portion are detected, for example, it is determined that the place of disconnection is in the inspiratory circuit 12. When the carbon dioxide concentration is smaller than a predetermined threshold, and lowering of the airway pressure to or below a predetermined value, and pulses of an amplitude (P-P value) equal to or smaller than a predetermined value in the lowered portion are detected, for example, it is determined that the place of disconnection is in the expiratory circuit 13.

Figure 8A:
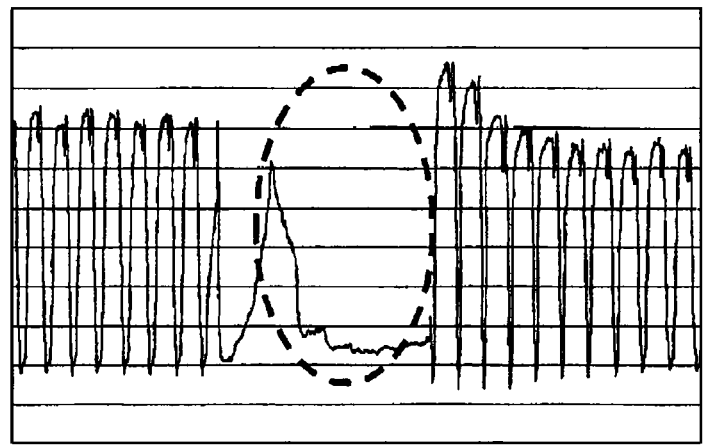
FIG. 8A shows the waveform of the carbon dioxide concentration in the case where a water trap is loosened in the second embodiment of the artificial ventilation apparatus of the invention.
Figure 8B:
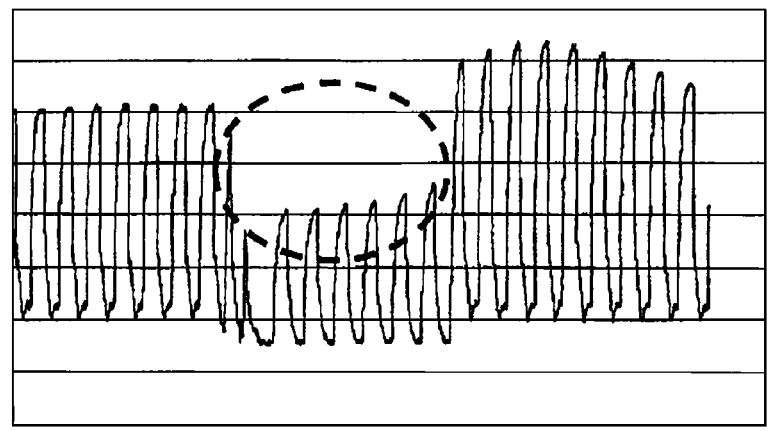
FIG. 8B shows the waveform of the airway pressure obtained in the embodiment.

Next, the case where a gas leak occurs due to loosening of the connecting portion of the water trap 44 of the expiratory circuit 13 will be described. FIGS. 8A and 8B show waveforms of the carbon dioxide concentration (FIG. 8A) and the airway pressure (FIG. 8B). In the graphs, the abscissa indicates the elapsed time. In this case, with respect to the carbon dioxide concentration, a rectangular wave due to respiration is disturbed and has a waveform which remains at a low level as indicted by the enclosing circle in FIG. 8A. From only the waveform of the carbon dioxide concentration, it is difficult to identify the place in the respiratory circuit where a trouble occurs.

By contrast, with respect to the airway pressure, a waveform having an amplitude (P-P value) which is about one half of that in a usual state is formed as indicted by the enclosing circle in FIG. 8B. When the amplitude (P-P value) of the waveform is within a predetermined range and the waveform of the carbon dioxide concentration is smaller than a predetermined threshold value as indicted by the enclosing circle in FIG. 8A, the controller 131 determines that a leak occurs in the expiratory circuit 13.

As seen from FIGS. 7A to 8B, the amplitude (P-P value) of the airway pressure when an abnormality occurs in the expiratory circuit 13 is small in the case where the expiratory circuit 13 is disconnected, and large in the case where a gas leak occurs due to loosening of the connecting portion of the water trap 44. Therefore, the degree of the abnormality can be estimated depending on the level of the amplitude (P-P value) of the airway pressure.

In place of the airway pressure, one of the following parameters may be used: the inspiratory and expiratory volumes per respiration; the peak inspiratory and expiratory flow rates per respiration; and the lung compliance.

In the second embodiment, the disconnected portion in the respiratory circuit is identified based on the carbon dioxide concentration and the airway pressure. The following information can be obtained based on the carbon dioxide concentration and the following parameters. In the case where the carbon dioxide concentration which is detected by the carbon dioxide concentration sensor 16 shows an abnormal value, it can be determined whether the abnormal value is caused by an accident or by an intentional operation, based on information of an alarm temporary release. Therefore, it is possible to prevent an erroneous alarm from being issued.

In the case where the carbon dioxide concentration shows an abnormal value, when the lung compliance is normal, and the alarm is not in a temporarily released state, it is estimated that the state is esophageal intubation. In place of the above-described lung compliance, a lung compliance which is calculated from the inspiratory and expiratory volumes per respiration, the peak inspiratory and expiratory flow rates per respiration, and the airway pressure may be used.

As described above, the apparatus state and the patient state can be obtained by using the carbon dioxide concentration sensor, and at least one of apparatus information of the artificial ventilation apparatus and biological information of the patient, and the operational management of the apparatus and monitoring of the patient can be performed more stably.

According to an aspect of the invention, the carbon dioxide concentration sensor which detects the carbon dioxide concentration is connected to the circuit that is downstream of the expiratory valve. Even when the carbon dioxide concentration sensor is contaminated, therefore, contamination toward the patient is blocked by the expiratory valve. Consequently, the frequencies of sterilization and replacement of the carbon dioxide concentration sensor are remarkably reduced. Therefore, the carbon dioxide concentration sensor can be firmly attached, resulting in that a work of checking the state of the attachment of the carbon dioxide concentration sensor is not necessary, the work of inspecting connecting portions between the ventilator and the patient is lightened, and furthermore the probability of disconnection of the connecting portions is decreased, thereby enhancing the safety.

According to an aspect of the invention, the carbon dioxide concentration sensor is connected to the circuit that is downstream of the expiratory valve. Therefore, the sensor is remote from the moisture generation source (a heating and humidifying device, the patient, or the like), and dew condensation scarcely occurs. Consequently, the carbon dioxide concentration can be accurately detected.

According to an aspect of the invention, the carbon dioxide concentration sensor is connected to the circuit that is downstream of the expiratory valve. In the case where, in a state where the patient performs spontaneous respiration, the expiratory circuit of the respiratory circuit on the upstream side of the carbon dioxide concentration sensor is disconnected, the expiratory of the patient does not normally reach the carbon dioxide concentration sensor, and hence the disconnection of the expiratory circuit can be detected. In the case where the inspiratory circuit is disconnected in a state where the patient performs spontaneous respiration, the disconnection may be detected depending on the place where the disconnection occurs. Specifically, when the place of the disconnection is on the downstream side (on the side which is close to the patient) of the inspiratory circuit, the expiratory of the patient leaks from the disconnection place, and does not reach the carbon dioxide concentration sensor, and hence the detection value of the carbon dioxide concentration sensor becomes abnormal, so that the disconnection of the inspiratory circuit can be detected. In the case where, in a state where the patient does not perform spontaneous respiration, the expiratory circuit of the respiratory circuit is disconnected, the respiratory gas does not reach the carbon dioxide concentration sensor irrespective of the disconnection place, and hence the detection value of the carbon dioxide concentration sensor becomes abnormal, so that the disconnection of the expiratory circuit can be detected. In the cased where the inspiratory circuit of the respiratory circuit is disconnected, the respiratory gas is not sent to the patient, and hence the detection value of the carbon dioxide concentration sensor becomes abnormal, so that the abnormal state can be detected similarly with a related-art apparatus.

According to an aspect of the invention, the apparatus includes the dedicated power supply portion which supplies the electric power to the carbon dioxide concentration sensor and the alarm outputting unit. Even when the power supply to the ventilator is stopped for any cause, or when, in a ventilator which does not include a carbon dioxide concentration sensor, a carbon dioxide concentration sensor is added in future, therefore, the carbon dioxide concentration sensor operates, and in case of necessary an alarm is generated, so that the abnormality can be known.

According to an aspect of the invention, the carbon dioxide concentration sensor is disposed in the exhaust port of the exhaust portion. With or without spontaneous respiration of the patient, therefore, it is possible to detect disconnection of the expiratory circuit of the respiratory circuit on the upstream side of the carbon dioxide concentration sensor. Consequently, it is possible to detect all kinds of disconnection of the expiratory circuit. Moreover, space limitations are not largely imposed on the apparatus. Even when a carbon dioxide concentration sensor is to be added in future, therefore, the sensor can be attached relatively easily.

According to an aspect of the invention, at least one of apparatus information of the artificial ventilation apparatus and biological information of the patient is obtained, and at least one of the apparatus state and the patient state is determined based on the obtained information and the output of the carbon dioxide concentration sensor. Therefore, the apparatus state and the patient state can be obtained, and the operational management of the apparatus and monitoring of the patient can be performed more stably.

What is claimed is:

1. An artificial ventilation apparatus comprising:
   a connecting portion which is adapted to be connected to a respiratory system of a patient;
   an inspiratory circuit which is a flow path for flowing a gas from a ventilator to the connecting portion;
   a first power supply which is configured to convert alternating current from an external power supply to direct current for supplying power to the ventilator;
   an expiratory circuit which is a flow path for guiding a gas exhausted from the connecting portion to an exhaust portion of the ventilator;
   an expiratory valve which blocks a flow of a gas from the exhaust portion toward the connecting portion;
   a carbon dioxide concentration sensor which is disposed in a circuit that is provided at a downstream side of the expiratory valve and which detects a carbon dioxide concentration;
   an alarm outputting unit which outputs an alarm based on an output of the carbon dioxide concentration sensor; and
   a second power supply which is configured to convert alternating current from the external power supply to direct current for supplying electric power to the carbon dioxide concentration sensor,
   wherein the ventilator receives power from the first power supply and not the second power supply,
   wherein the first power supply and the second power supply are distinct components spatially separated from one another, and
   wherein a functioning abnormality of one of the first power supply and the second power supply does not result in a functioning abnormality of the other of the first power supply and the second power supply.

2. The artificial ventilation apparatus according to claim 1, wherein the second power supply supplies electric power to the alarm outputting unit.

3. The artificial ventilation apparatus according to claim 1, wherein the carbon dioxide concentration sensor is disposed in an exhaust port of the exhaust portion.

4. The artificial ventilation apparatus according to claim 1, wherein the alarm outputting unit includes a state determining unit which obtains information, which includes at least one of apparatus information of the artificial ventilation apparatus and biological information of the patient, the state determining unit which, based on obtained information and the output of the carbon dioxide concentration sensor, determines whether a state, which includes at least one of an apparatus state of the artificial ventilation apparatus and a patient state of the patient, is abnormal or not.

* * * * *